United States Patent [19]

Wiechert et al.

[11] Patent Number: 4,891,365
[45] Date of Patent: Jan. 2, 1990

[54] 17-SUBSTITUTED ESTRADIENES AND ESTRATRIENES

[75] Inventors: Rudolf Wiechert; Sybille Beier; Walter Elger, all of Berlin; Klaus Annen, Muenster-Albachten; Klaus Nickisch; Henry Laurent, both of Berlin, all of Fed. Rep. of Germany

[73] Assignee: Schering Aktiengesellschaft, Berlin and Bergkamen, Fed. Rep. of Germany

[21] Appl. No.: 69,061

[22] Filed: Jul. 2, 1987

Related U.S. Application Data

[63] Continuation of Ser. No. 714,420, Mar. 21, 1985, abandoned.

[30] Foreign Application Priority Data

Mar. 21, 1984 [DE] Fed. Rep. of Germany ....... 3410880

[51] Int. Cl.[4] .................. A61K 31/58; A61K 31/585; A61K 31/56; C07J 1/00
[52] U.S. Cl. ................................... 514/173; 514/175; 514/178; 514/179; 540/15; 540/28; 540/41; 260/397.4; 260/397.45
[58] Field of Search ............................ 540/15, 28, 41; 260/397.4, 397.45; 514/173, 175, 178, 179

[56] References Cited

U.S. PATENT DOCUMENTS 4,536,401 8/1985 Neef et al. ...................... 260/397.45
4,540,686 9/1985 Philibert et al. ..................... 514/179

Primary Examiner—Douglas W. Robinson
Assistant Examiner—Joseph A. Lipovsky
Attorney, Agent, or Firm—Millen, White & Zelano

[57] ABSTRACT

17-Substituted estradienes and estratrienes of Formula I

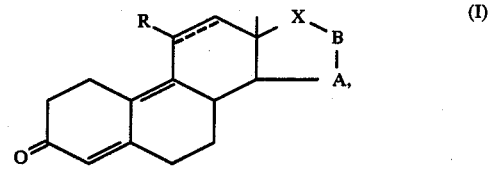

wherein

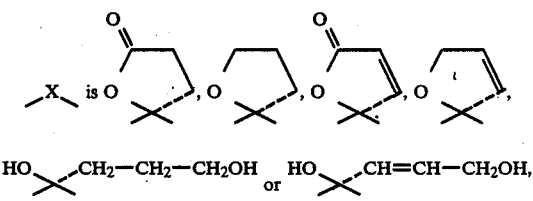

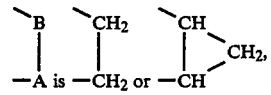

$R$ is alkyl, alkenyl or cycloalkyl of up to 5 carbon atoms if

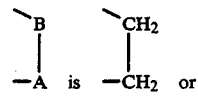

$R$ is hydrogen, alkyl, alkenyl or cycloalkyl of up to 5 carbon atoms if

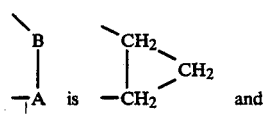 and

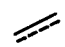

is a CC-single or CC-double bond, exhibit, an aldosterone-antagonistic activity and a strong gestagen potency.

27 Claims, No Drawings

17-SUBSTITUTED ESTRADIENES AND ESTRATRIENES

This is a continuation of application Serial No. 714,420 filed Mar. 21, 1985 now abandoned.

BACKGROUND OF THE INVENTION

This invention relates to 17-substituted estradienes and estratrienes, processes for their preparation and pharmaceutical preparations containing them.

Estradienes without a substitute in the 11-and/or 15,16-position are known from U.S. Pat. Nos. 3,509,135, 3,238,197 and 3,764,596. These compounds exhibit aldosterone-antagonistic and gestagen activity.

French Patent No. 1,453,222 discloses estratrienes unsubstituted in the 11-and 15,16-positions displaying antialdosterone activity.

SUMMARY OF THE INVENTION

It is an object of this invention to provide new compounds having valuable pharmacological properties.

Upon further study of the specification and appended claims, further objects and advantages of this invention will become apparent to those skilled in the art.

These objects have been achieved by providing 17-substituted estradienes and estratrienes of Formula I

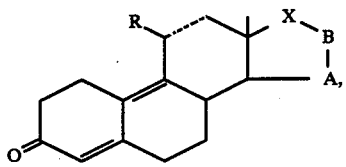

wherein

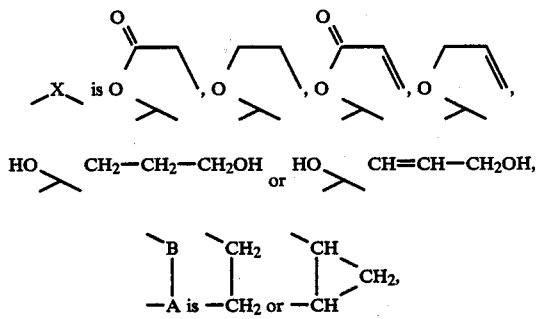

R is alkyl, alkenyl or cycloalkyl of up to 5 carbon atoms if

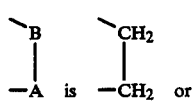

R is hydrogen, alkyl, alkenyl or cycloalkyl of up to 5 carbon atoms if

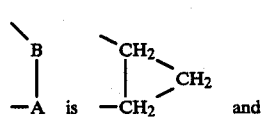

and is a CC-single or CC-double bond.

DETAILED DISCUSSION OF THE INVENTION

The novel compounds of Formula I have, besides a high aldosterone-antagonistic effect, a strong gestagen potency. Since the novel compounds possess the progesterone-like profile of activity, the side effects that otherwise occur, such as blood pressure increase and edemas, will not occur when these compounds are utilized as contraceptives.

It has been found that the novel compounds of Formula I, substituted in the 11-and/or 15,16-position, are superior to the heretofore known compounds of this class of substances. The 11β-alkyl, alkenyl or cycloalkyl substituent effects a rise in gestagen activity, and the 15,16-methylene group effects an enhancement of aldosterone-antagonistic effect.

In a test for antialdosterone activity, the novel compounds have proven to be equal in efficacy to the conventional spironolactone. In the gestagen receptor binding test for gestagen activity, using cytosol from rabbit uterus homogenate and employing $^3$H-progesterone as the reference compound, the novel compounds show a strong affinity to the gestagen receptor and, in the Clauberg test, show great efficacy upon subcutaneous administration of 0.3 mg, whereas spironolactone shows minimum effect on the endometrium and only at 50 mg.

The following table shows the competition factors (C) in the gestagen receptor binding test. The competition factor C, as a standard for the binding strength, is defined as the ratio of concentration of test compound to concentration of standard (progesterone) at which both compounds display equally strong displacement of $^3$H-progesterone from the progesterone receptor complex, so that a low C value indicates high binding strength (high affinity).

The McPhail values are also shown, as obtained in the Clauberg test for gestagen activity. Castrated female rabbits daily receive 5 μg of estradiol subcutaneously over a period of 6 days. From the 7th to 11th day, the compound to be tested is administered once daily subcutaneously. On the twelfth day, the animals are sacrificed, and the uterine horns are excised and examined histologically. In the histological sections, the secretory transformation of the endometrium is determined. Determination takes place according to the McPhail scale (evaluation grades 1-4; 1=no transformation; 4=complete transformation). The threshold value is considered to be the smallest dose at which, in the group average, a McPhail value of 1.5 is attained.

TABLE

| Compound | Gestagen Receptor Binding Test C (Gestagen) | Clauberg Test s.c. Dose [mg] | McPhail Value |
|---|---|---|---|
| A | 0.5 | 0.3 | 2.7 |
| B | 0.5 | | |
| C | 0.4 | 0.3 | 2.5 |
| D | 1.0 | | |

A: 19-Nor-3-oxo-11β-vinyl-17α-pregna-4,9-diene-21,17-carbolactone
B: 11 β-Methyl-15β,16β-methylene-3-oxo-19-nor-17α-pregna-4,9-diene-21,17-carbolactone
C: 11 β-Methyl-19-nor-3-oxo-17α-pregna-4,9-diene-21,17-carbolactone
D: 11β-Ethyl-19-nor-3-oxo-17α-pregna-4,9-diene-21,17-carbolactone The novel compounds of Formula I can be utilized by themselves or in combination with estrogens in preparation for contraception. According to this invention, the novel compounds are particularly useful for women desiring contraception who also are prone to hypertension because of risk factors present, e.g., advanced age, obesity, smoking, etc. Considering the profile of these compounds which is comparable to that of natural progesterone, they are apt to improve subjective well-being and compatibility over conventional preparations even in women who cannot be classified as high-risk patients.

The dosage of the compounds of this invention in contraceptive preparations preferably is 0.5–5 mg per day. The gestagen and estrogen active agent components are preferably administered orally in contraceptive preparations in combined form. The daily dose is preferably administered all at once. The estrogen is preferably administered in a quantity corresponding to 0.03–0.05 mg of ethynylestradiol. For contraceptive purposes, the compounds of this invention are employed analogously to that of the conventional agent norhestrel, e.g., as it is used in the conventional product Ovral(R).

The novel compounds of Formula I can also be utilized in preparations for the treatment of gynecological disorders. On account of their favorable activity profile, the compounds of this invention are especially well suited for the treatment of premenstrual complaints, such as headaches, depressions, water retention and mastodynia. The daily dose when treating premenstrual difficulties is preferably about 1–20 mg, analogously to Duoluton(R).

The pharmaceutical preparations based on the novel compounds can be formulated conventionally by processing the active agent, optionally in combination with an estrogen, with the excipients, diluents, if desired flavoring agents, etc., customary in galenic pharmacy, and converting this preparation into the desired form of administration. Tablets, degrees, capsules, pills, suspensions or solutions are especially suitable for the preferred oral administration. Particularly suited for parenteral administration are oily solutions, e.g., solutions in sesame oil, castor oil and cottonseed oil. To enhance solubility, solubilizers can be added, such as, for example, benzyl benzoate or benzyl alcohol.

The pharmacologically active compounds of this invention can be processed in accordance with conventional methods of galenic pharmacy to produce medicinal agents for administration to patients, e.g., mammals, including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

Generally, the compounds of this invention are dispensed in unit dosage form comprising 0.5–5.0 mg in a pharmaceutically acceptable carrier per unit dosage.

Dosages for a given host can be determined using conventional considerations, e.g., by customary comparison of the differential activities of the subject compound and of a known agent, e.g., by means of an appropriate, conventional pharmacological protocol.

The novel 17-substituted estradienes and estratrienes of general Formula I contain in the 11-position hydrogen or an alkyl, alkenyl or cycloalkyl group of up to 5 carbon atoms. Alkyl includes, for example, methyl, ethyl, propyl, isopropyl, a butyl group, a pentyl group, etc.; alkenyl includes the corresponding unsaturated alkyl groups, for example, vinyl and 2-propenyl; cycloalkyl includes, for example, cyclopropyl, cyclobutyl and cyclopentyl. The methyl, ethyl and vinyl groups are preferred.

The novel compounds of general Formula I can be prepared conventionally according to this invention by a process for the preparation of 17-substituted estradienes and estratrienes of Formula I

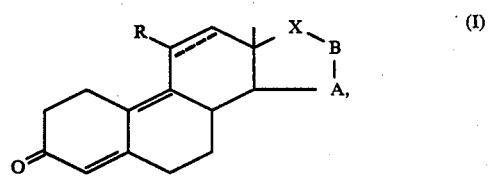

wherein

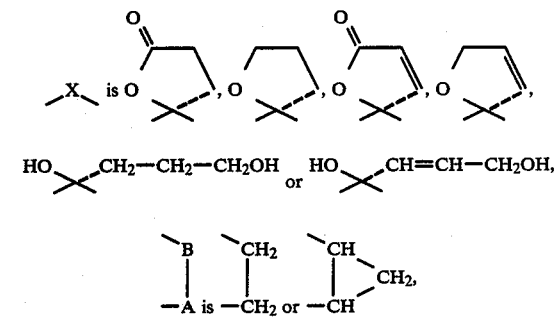

R is alkyl, alkenyl or cycloalkyl of up to 5 carbon atoms if

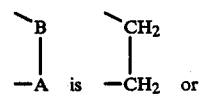

R is hydrogen, alkyl, alkenyl or cycloalkyl of up to 5 carbon atoms if

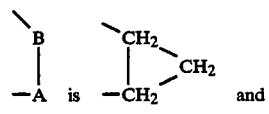

is a CC-single or CC-double bond, comprising conventionally (a) treating a compound of Formula II

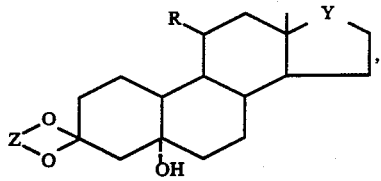

wherein
R has the meanings given for Formula I,
Y stands for X wherein any present free hydroxy groups can be etherified with a group that can be readily split off under acidic conditions and
Z is an ethylene or 2,2-dimethylpropylene group, with a dilute acid, the pyridinium salt of a strong acid or with an acidic ion exchanger, for ketal cleavage, for removal of any blocking group that can be present and may be split off with an acid and for simultaneously splitting off water with the formation of the 4,9-dien-3-one system; and optionally cyclizing the thus-obtained 17α-(3-hydroxypropyl)- or 17α-(3-hydroxypropenyl)-compound to the 17-spiro-hydrofuran compound or oxidizing this compound to the 21,17-carbolactone; and, if desired, introducing the Δ$^{11}$-double bond; or (b) treating a compound of Formula III

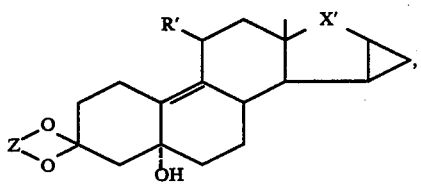

wherein
R' is alkyl, alkenyl or cycloalkyl of up to 5 carbon atoms,

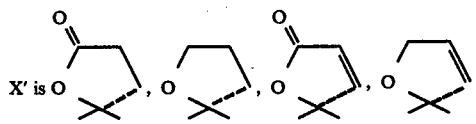

and
Z is an ethylene or 2,2-dimethylpropylene group, with a dilute acid, the pyridinium salt of a strong acid or with an acidic ion exchanger, for ketal cleavage and for simultaneously splitting off water under formation of the 4,9-dien-3-one system; and optionally reducing the thus-obtained 21,17-carbolactone to the 17α-(3-hydroxoypropyl)- or 17α-(3-hydroxypropenyl)-compound, reoxidizing the concomitantly reduced 3-keto group with manganese dioxide and optionally introducing the Δ$^{11}$-double bond; or (c) treating a compound of Formula IV

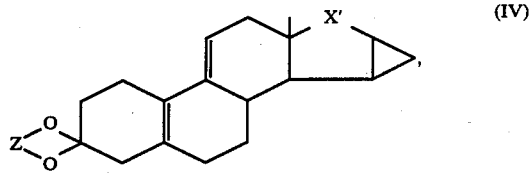

wherein X' and Z have the meanings given in Formula III, with an acid for ketal cleavage with formation of the 4,9-dien-3-one system and optionally reducing the thus-obtained 21,17-carbolactone to the 17α-(3-hydroxypropyl)- or 17α-(3-hydroxypropenyl)-compound and reoxidizing the concomitantly reduced 3-keto group with manganese dioxide and, if desired, introducing the Δ$^{11}$-double bond; or (d) hydrogenating or reducing a compound of Formula V

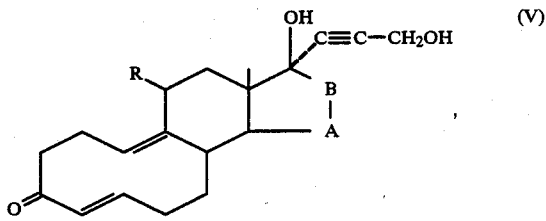

wherein

and R have the meanings given in Formula I, to the 17α-(3-hydroxypropenyl)-compound; cyclizing the latter optionally to the corresponding 17-spiro-hydrofuran compound or oxidizing the same to the corresponding 21,17-carbolactone, and optionally introducing the Δ$^{11}$-double bond.

In order to split a ketal in the foregoing, remove a hydroxy blocking group that may be present in the 22-position and split off water to obtain the 4,9-diene-3-ketone, a compound of general Formula II or III is treated with an acid, the pyridinium salt of a strong acid or an acidic ion exchanger. The hydroxy blocking group that can be readily split off in an acidic medium is, for example, a methoxymethyl, ethoxymethyl or tetrahydropyranyl group.

The acid treatment takes place conventionally by dissolving a compound of general Formula II or III in a water-miscible solvent, such as aqueous methanol, ethanol or acetone, and treating the solution with catalytic amounts of a mineral acid or sulfonic acid, such as hydrochloric acid, sulfuric acid, perchloric acid or p-toluenesulfonic acid until the cleavage of ketal and water and the splitting off of any present acid-sensitive blocking groups have been completed. The reaction, taking place at temperatures of about 20°–100° C., can also be performed in an especially high yield with a pyridinium salt, such as pyridinium tosylate, or with an acidic ion exchanger.

The course of the reaction is suitably controlled by analytical methods, e.g., by thin-layer chromatography of withdrawn samples.

A 17α-(3-hydroxypropyl)- or 17α-(3-hydroxypropenyl)compound of Formula I, obtained according to process (a) or (d), can subsequently be conventionally cyclized to the corresponding 17-spiro-hydrofuran compound of Formula I or oxidized to the corresponding 21,17-carbolactone of Formula I. The oxidation is carried out with the customary oxidizing agents, e.g., Jones reagent, chromic acid-pyridine, pyridinium dichromate or pyridinium chlorochromate. Cyclizing takes place with agents splitting off water, for example, with p-toluenesulfonic acid chloride in the presence of pyridine.

A 21,17-carbolactone of Formula I obtained by process (b) or (c) can subsequently be reduced in a manner known per se to the 17α-(3-hydroxypropyl)- or 17α-(3-hydroxypropenyl)-compound of Formula I. Suitable for reduction are, for example, metallic hydrides, such as lithium aluminum hydride. The concomitantly reduced 3-keto group can thereafter be reoxidized with manganese dioxide.

The optionally following introduction of the $\Delta^{11}$-double bond takes place according to the process known to persons skilled in the art by dehydrogenation of corresponding $\Delta^{5(10),9(11)}$-steroids. Rearrangement of the 4,9-dien-3-one system into the 5(10),9(11)-dien-3-one system is effected by ketalizing and deketalizing under gentle conditions.

For ketalizing with shifting of the double bonds, the 3-ketone is treated with an alkylene diol, such as ethylene glycol or 2,2-dimethylpropanediol in the presence of a dehydrating agent, such as trimethyl orthoformate, and a mineral or sulfonic acid. Splitting of the ketal, resulting in the $\Delta^{5(10),9(11)}$-diene system, takes place in aqueous acetic, oxalic or pyruvic acid at room temperature.

Dehydrogenation can be performed conventionally with dehydrogenating agents. Suitable dehydrogenating agents include, for example, selenium dioxide and substituted p-quinones, especially substituted p-benzoquinones, such as 2,3-dichloro-5,6-dicyanobenzoquinone (DDQ), 2,3-dibromo-5,6-dicyanobenzoquinone, 2,3-dicyano-4-chlorobenzoquinone, 2,3-dicyanobenzoquinone and 2,3,5,6-tetrachlorobenzoquinone (chloranil). Dehydrogenation is carried out suitably, in an organic solvent, e.g., with substituted quinones in methylene chloride, dichloroethane, chlorobenzene, benzene, toluene, dioxane, ethyl acetate, diethyl ether, ethylene glycol, dimethylformamide, nitrobenzene, dimethyl sulfoxide, etc. The reaction can take place at room temperature or under elevated temperature; preferably, the reaction is performed under an inert gas at room temperature. The dehydrogenation of $\Delta^{5(10),9(11)}$-steroids with substituted quinones to $\Delta^{4,9,11}$-steroids has been described in detail in U.S. Pat. No. 3,453,267, which document is incorporated by reference herein. Dehydrogenation with selenium dioxide is conducted, for example, in dioxane under boiling heat.

According to process (c), ketal splitting of a compound of Formula IV with formation of the 4,9-dien-3-one system is conventionally performed with an organic or inorganic acid.

The compound of Formula IV is heated in a water-miscible solvent, such as aqueous methanol, ethanol or acetone, with an organic acid, such as acetic acid or oxalic acid, or a mineral or sulfonic acid, such as hydrochloric acid, sulfuric acid, phosphoric acid, perchloric acid or p-toluenesulfonic acid. The ketal splitting reaction, occurring at temperatures of about 20° to 100° C., can be controlled by analytical methods, e.g., with the aid of thin-layer chromatography.

According to process (d), the triple bond of the 17α-(3-hydroxypropynyl)-compound of Formula V is hydrogenated or reduced, respectively, to the Z- or E-configured double bond, respectively.

The compound with the Z-configured double bond is formed by hydrogenation of the acetylenic triple bond in the presence of a deactivated noble metal catalyst (J. Fried, J. A. Edwards: Organic Reactions in Steroid Chemistry, Van Nostrand Reinhold Company, 1972, p. 134; and H. O. House: Modern Synthetic Reactions, 1972, p. 19). Deactivated noble metal catalysts can be, for example, 10% palladium on barium sulfate in the presence of an amine or 5% palladium on calcium carbonate with the addition of lead(II) acetate according to Lindlar. Hydrogenation is terminated after absorption of one equivalent of hydrogen.

The compound with the E-configured double bond is formed by reduction of the acetylenic triple bond in a manner known, per se. Quite a number of methods have been described in the literature for the conversion of alkynes into trans-olefins, for example, reduction with sodium in liquid ammonia (J. Am. Chem. Soc. 63:216[1941], with sodium amide in liquid ammonia (J. Chem. Soc. 1955:3558), with lithium in low-molecular amines (J. Am. Chem. Soc. 77:3378[1955], with boranes (J. Am. Chem. Soc. 93:3395[1971] and 94:6560[1971]), with diisobutyl aluminum hydride and methyllithium (J. Am. Chem. Soc. 89:5085[1967]) and especially with lithium aluminum hydride/alcoholate (J. Am. Chem. Soc. 89:4245[1967]).

Another possibility is reducing the triple bond with chromium(II) sulfate in the presence of water or dimethylformamide in a weakly acidic medium (J. Am. Chem. Soc. 86:4358[1964]) and generally reducing by treatment with transition metal compounds with a change in oxidation stage.

All of the starting materials described above are known or are conventionally preparable from known materials using fully conventional processes. Their preparation is exemplified below.

The starting compounds for the preparation of starting materials of Formulae II-V are described in European patent Applications Nos. 82400025.(publication No. 0057115) and No. 84101721.3 (publication No. 011697).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

PREPARATION OF THE STARTING COMPOUNDS OF GENERAL FORMULA II

Direction 1

Under argon, 238 mmol of n-butyllithium is added dropwise to a solution of 25 g of propargyl alcohol tetrahydropyranyl ether in 500 ml of tetrahydrofuran (THF) and the mixture is stirred for 15 minutes. Then 16.6 g of 3,3(2,2-dimethylpropylene-1,3-dioxy)-5α,10α-epoxy-9(11)-estren-17-one in 300 ml of THF is added dropwise thereto and the mixture stirred for another 30 minutes. Subsequently the mixture is precipitated into 3.5 l of ice water, extracted with ethyl acetate and washed neutral with water. Chromatography on aluminum oxide yields 26 g of 3,3-(2,2-dimethyltrimethylenedioxy)-5α,10α-epoxy-17α-(tetrahydropyranyloxypropynyl)-9(11)-estren-17β-ol.

A solution of 15.4 g of 3,3-(2,2-dimethyltrimethylenedioxy)-5α,10α-epoxy-17α-tetrahydropyranyloxypropynyl)-9(11)-estren-17β-ol in 200 ml of THF is hydrogenated with 3 g of tris-triphenylphosphine rhodium(I) chloride. After absorption of 1,350 ml of hydrogen, the mixture is concentrated under vacuum. The resultant crude product is chromatographed on aluminum oxide, yielding 13.8 g of 3,3-(2,2-dimethyltrimethylenedioxy)-5α,10α-epoxy-17α-(tetrahydropyranyloxy)propyl-9(11)-estren-17β-ol.

At −30° C., 150 mg of Cu$_2$Cl$_2$ is added to 95 ml of a 1.3-molar vinyl magnesium bromide solution and the mixture is agitated for 30 minutes at this temperature. A solution of 8.5 g of 3,3-(2,2-dimethyltrimethylenedioxy)-5α,10α-epoxy-17α-(tetrahydropyranyloxy)propyl-9(11)-estren-17β-ol in 100 ml of THF is added dropwise to this mixture and the latter is stirred for 2 hours at −20° C. Subsequently the mixture is poured into cold ammonium chloride solution, extracted with ether, washed with water, dried over sodium sulfate and concentrated under vacuum. The resultant crude product is chromatographed on aluminum oxide, thus obtaining 6.5 g of 3,3-(2,2-dimethyltrimethylenedioxy)-11β-vinyl-17α(3-tetrahydropyranyloxy)propyl-9-estrene-5α,17β-diol.

Direction 2

At −30° C., 100 mg of Cu$_2$Cl$_2$ is added to a Grignard solution prepared from 1.3 g of magnesium and 6.57 g of 2-bromopropene in 100 ml of THF; the mixture is stirred for 30 minutes. To this mixture is added dropwise a solution of 2.78 g of 3,3-(2,2-dimethyltrimethylenedioxy)-5α,10α-epoxy-17α-[(3-tetrahydropyranyloxy)propyl]-9(11)-estren-17β-ol in 35 ml of THF and the mixture is agitated for 3 hours; during this step the temperature rises to 0° C. Subsequently the mixture is poured into ammonium chloride solution, extracted with ether, washed with water, dried and concentrated under vacuum. The resultant crude product is chromatographed on aluminum oxide, yielding 2.4 g of 3,3-(2,2-dimethyltrimethylenedioxy)-11β-isopropenyl-17α-(3-tetrahydropyranyloxy)propyl-9-estrene-5α,17β-diol.

Direction 3

At −30° C., 150 mg of copper(I) chloride is added to a Grignard solution prepared from 7.07 g of magnesium and 18.2 ml of methyl iodide in 440 ml of ether; the mixture is stirred for 30 minutes at this temperature. A solution of 10 g of 3,3-(2,2-dimethyltrimethylenedioxy)-5α,10α-epoxy-17α-[(3-tetrahydropyranyloxy)propyl]-9(11)-estren-17β-ol in 100 ml of ether is added dropwise to this mixture and the latter is stirred for 30 minutes at this temperature. Subsequently the mixture is poured into ammonium chloride solution, extracted with ether, washed with water and dried over sodium sulfate. The resultant crude product is chromatographed on aluminum oxide, thus obtaining 7.8 g of 3,3-(2,2-dimethyltrimethylenedioxy)-11β-methyl-17α-[(3-tetrahydropyranyloxy)propyl]-9-estrene-5α,17β-diol.

Direction 4

Under the conditions given in direction (3), 5 g of 3,3-(2,2-dimethyltrimethylenedioxy)-5α,10α-epoxy-17α[(3-tetrahydropyranyloxy)propyl]-9(11)-estren-17β-ol and ethylmagnesium bromide yield 3.4 g of 3,3-(2,2-dimethyltrimethylenedioxy)-11β-ethyl-17α-[(3-tetrahydropyranyloxy)propyl]-9-estrene-5α,17β-diol.

Direction 5

Under the conditions described in direction (3), 4 g of 3,3-(2,2-dimethyltrimethylenedioxy)-5α,10α-epoxy-17α[(3-tetrahydropyranyloxy)propyl]-9(11)-estren-17β-ol and propylmagnesium bromide yield 2.2 g of 3,3-(2,2-dimethyltrimethylenedioxy)-11β-propyl-17α-[(3-tetrahydropyranyloxy)propyl]-9-estrene-5α,17β-diol.

Direction 6

Under the conditions set forth in direction (3), 4.5 g of 3,3-(2,2-dimethyltrimethylenedioxy)-5α,10α-epoxy-17α-[(3-tetrahydropyranyloxy)propyl]-9(11)-estren-17β-ol and cyclopropylmagnesium bromide yield 2.9 g of 11β-cyclopropyl-3,3-(2,2-dimethyltrimethylenedioxy)-17α-[(3-tetrahydropyranyloxy)propyl]-9-estrene-5α,17β-diol.

Direction 7

Under the conditions described in direction (3), 1.2 g of 3,3-(2,2-dimethyltrimethylenedioxy)-5α,10α-epoxy-17α-[(3-tetrahydropyranyloxy)propyl]-9(11)-estren-17β-ol yields 750 mg of 11β-cyclopentyl-3,3-(2,2-dimethyltrimethylenedioxy)-17α-[(3-tetrahydropyranyloxy)propyl]-9-estrene-5α,17β-diol.

Direction 8

(a) Under the conditions described in direction (3), 2.5 g of 3,3-(2,2-dimethyltrimethylenedioxy)-5α,10α-epoxy-9(11)-estren-17-one yields 1.5 g of 11β-cyclopropyl-3,3-(2,2-dimethyltrimethylenedioxy)-5α-hydroxy-9-estren-17-one.

(b) Under the conditions disclosed in direction (1), 1 g of 11β-cyclopropyl-3,3-(2,2-dimethyltrimethylenedioxy)-5α-hydroxy-9-estren-17-one yields 1.3 g of 11β-cyclopropyl-3,3-(2,2-dimethyltrimethylenedioxy)-17-[3-(tetrahydropyranyloxy)-1-propynyl]-9-estrene-5α,17β-diol.

(c) A solution of 1.2 g of 11β-cyclopropyl-3,3-(2,2-dimethyltrimethylenedioxy)-17-[3-(tetrahydropyranyloxy)-1-propynyl]-9-estrene-5α,17β-diol in 12 ml of anhydrous ethanol is hydrogenated with 60 mg of Lindlar catalyst for 5 hours at room temperature. After removing the catalyst by filtration, the mixture is concentrated and the resultant crude product is purified by chromatography on silica gel, thus producing 750 mg of 11β-cyclopropyl-3,3-(2,2-dimethyltrimethylenedioxy)-17-[3-(tetrahydropyranyloxy)]-1-(Z)-propenyl-9-estrene-5α,17β-diol.

Preparation of the Starting Compounds of General Formula III

Direction 9

(a) A solution of 20 g of 15α-hydroxyestra-4,9-diene-3,17-dione in 120 ml of pyridine is combined dropwise with 13.6 ml of benzoyl chloride and the mixture is stirred for one hour at room temperature. Subsequently the mixture is poured into ice water, extracted with dichloromethane, washed with sodium bicarbonate solution and water and concentrated under vacuum. The cooled crude product is chromatographed on silica gel, yielding 26.2 g of 15α-benzoyloxyestra-4,9-diene-3,17-dione.

(b) A solution of 8.7 g of trimethylsulfoxonium iodide in 200 ml of dimethyl sulfoxide (DMSO) is agitated with 1.625 g of 55% strength sodium hydride for one hour. To this mixture is added 4.9 g of 15α-benzoyloxyestra-4,9-diene-3,17-dione, the mixture is agitated for 10 minutes and then poured into ice water. Then the aqueous phase is extracted with dichloromethane and the thus-obtained crude product is purified by column chromatography on silica gel, yielding 2.07 g of 15β,16β-methylene-estra-4,9-diene-3,17dione.

IR 1710, 1660, 1580 cm$^{-1}$.
UV: $\epsilon_{302}$=20,000.

(c) A solution of 10 g of 15β,16β-methylene-estra-4,9-diene-3,17-dione in 25 ml of dichloromethane is stirred at room temperature for 20 minutes with 10 g of 2,2-dimethyl-1,3-propanediol, 12.7 ml of triethyl orthoformate and 125 g of p-toluenesulfonic acid. Subsequently the mixture is combined with triethylamine and washed with water. After evaporation, the resultant crude product is chromatographed on silica gel, yielding 8.20 g of 3,3-(2,2-dimethyltrimethylenedioxy)-15β,16β-methylene-estra-5(10),9(11)-dien-17-one, mp 159.6° C.

IR: 1710 cm$^{-1}$.
UV: $\epsilon_{242}$=18,500.
$[\alpha]_D$=+223°.

(d) A solution of 32.2 g of 3,3-(2,2-dimethyltrimethylenedioxy)-15β,16β-methylene-estra-5(10),9(11)-dien-17-one in 200 ml of dichloromethane is combined under ice cooling in succession with 1.26 ml of hexachloroacetone and 14.5 ml of 30% strength hydrogen peroxide and stirred for 24 hours at room temperature. The mixture is then washed with sodium thiosulfate solution and water, dried and concentrated. The thus-obtained crude product is chromatographed on aluminum oxide, thus producing 17.5 g of 3,3-(2,2-dimethyltrimethylenedioxy)-5α,10α-epoxy-15β,16β-methylene-estr-9(11)-en-17-one, mp 173.4° C.

(e) A solution of 11.4 g of 3,3-(2,2-dimethyltrimethylenedioxy)-5α,10α-epoxy-15β,16β-methylene-estr-9(11)-en-17-one in 200 ml of tetrahydrofuran (THF) is combined under ice cooling with 45.4 g of potassium ethylate and 17 ml of propargyl alcohol and stirred for 30 minutes. Then the mixture is poured into ice water, neutralized with sulfuric acid, extracted with ethyl acetate, washed with water and concentrated under vacuum, yielding 12.1 g of 3,3-(2,2-dimethyltrimethylenedioxy)-5α,10α-epoxy-15β,16β-methylene-17α-(3-hydroxypropynyl)estr-9(11)-en-17β-ol.

(f) A solution of 11.9 g of 3,3-(2,2-dimethyltrimethylenedioxy)-5α,10α-epoxy-15β,16β-methylene-17α(3-hydroxypropynyl)estr-9(11)-en-17β-ol in 175 ml of THF is hydrogenated with 2.5 g of tris-triphenylphosphine rhodium(I) chloride. After absorption of 1,090 ml of hydrogen, the mixture is concentrated under vacuum and chromatographed on aluminum oxide, thus obtaining 9.7 g of 3,3-(2,2-dimethyltrimethylenedioxy)-5α,10α-epoxy-15β,16β-methylene-17α-(3-hydroxypropyl)estr-9(11)-en-17β-ol.

(g) Under the conditions described in direction (3), 6 g of 3,3-(2,2-dimethyltrimethylenedioxy)-5α,10α-epoxy-15β,16β-methylene-17α-(3-hydroxypropyl)estr-9(11)-en-17β-ol yields 3.9 g of 3,3-(2,2-dimethyltrimethylenedioxy)-11β-methyl-15β,16β-methylene-17α-(3-hydroxypropyl)estr-9-ene-5α,17β-diol.

(h) Under the conditions indicated in Example 3(b), 3.8 g of 3,3-(2,2-dimethyltrimethylenedioxy)-11β-methyl-15β,16β-methylene-17α-(3-hydroxypropyl)estr-9-ene-5α,17β-diol yields 2.8 g of 3,3-(2,2-dimethyltrimethylenedioxy)-5α-hydroxy-11β-methyl-15β,16β-methylene-19-nor-17α-pregn-9-ene-21,17-carbolactone.

IR 3350, 1760 cm$^{-1}$.

Direction 10

(a) Under the conditions set forth in direction (3), 5 g of 3,3-(2,2-dimethyltrimethylenedioxy)-5α,10α-epoxy-15β,16β-methylene-17α-(3-hydroxypropyl)estr-9(11)-en-17β-ol yields 2.7 g of 3,3-(2,2-dimethyltrimethylenedioxy)-5α-hydroxy-15β,16β-methylene-11β-vinyl-17α-(3-hydroxypropyl)estr-9-ene-5α,17β-diol.

(b) Under the conditions set forth in Example 3(b), 2.6 g of 3,3-(2,2-dimethyltrimethylenedioxy)-5α-hydroxy-15β,16β-methylene-11β-vinyl-17α-(3-hydroxypropyl)estr-9-ene-5α,17β-diol produces 1.9 g of 3,3-(2,2-dimethyltrimethylenedioxy)-5α-hydroxy-15β,16β-methylene-11β-vinyl-19-nor-17α-pregn-9-ene-21,17-carbolactone.

IR: 3350, 1760 cm$^{-1}$.

Direction 11

(a) Under the conditions described in direction (3), 4.5 g of 3,3-(2,2-dimethyltrimethylenedioxy) 5α,10α-epoxy-15β,16β-methylene-17α-(3-hydroxypropyl)estr-9(11)-en-17β-ol yields 3.15 g of 11β-cyclopropyl-3,3-(2,2-dimethyltrimethylenedioxy)-15β,16β-methylene-17α-(3-hydroxypropyl)estr-9-ene-5α,17β-diol.

(b) Under the conditions indicated in Example 3(b), 3.1 g of 11β-cyclopropyl-3,3-(2,2-dimethyltrimethylenedioxy)-15β,16β-methylene-17α-(3-hydroxypropyl)estr-9-ene-5α,17β-diol produces 1.9 g of 11β-cyclopropyl-3,3-(2,2-dimethyltrimethylenedioxy)-5α-hydroxy-15β,16β-methylene-19-nor-17α-pregn-9-ene-21,17-carbolactone.

IR: 3350, 1760 cm$^{-1}$.

The starting compounds of general Formulae IV and V are produced by analogous methods.

EXAMPLE 1

(a) A solution of 6.5 g of 3,3-(2,2-dimethyltrimethylenedioxy)-11β-vinyl-17α[(3-tetrahydropyranyloxy)propyl]-9-estrene-5α,17β-diol in 200 ml of 90% ethanol is combined with 50 mg of p-toluenesulfonic acid and agitated for 45 minutes at 75° C. The mixture is then poured in water, made alkaline with ammonia and extracted with dichloromethane. After washing and drying the product is concentrated under vacuum. The resultant crude product is chromatographed on silica gel, thus obtaining 3.2 g of 17β-hydroxy-17α(3-hydroxypropyl)-11β-vinyl-4,9-estradien-3-one.

IR: 3400, 1660, 1620 cm$^{-1}$.
UV: $\epsilon_{301}$=14,200.

(b) At −10° C., 16 ml of Jones solution is added dropwise to a solution of 3.2 g of 17β-hydroxy-17α-(3-hydroxypropyl)-11β-vinyl-4,9-estradien-3-one in 170 ml of acetone and the mixture is stirred for 30 minutes at this temperature. Subsequently the excess reagent is destroyed with methanol, the mixture is diluted with ethyl acetate and washed with water. After drying and concentrating, the resultant crude product is chromatographed on silica gel, thus obtaining 1.56 g of 19-nor-3- oxo-11β-vinyl-17α-pregna-4,9-diene-21,17-carbolactone, mp 133°–135° C.

EXAMPLE 2

(a) A solution of 2.2 g of 3,3-(2,2-dimethyltrimethylenedioxy)-11β-isopropenyl-17α-[3-(tetrahydropyranyloxy)propyl]-9-estrene-5α,17β-diol in 70 ml of 90% aqueous ethanol is combined with 20 mg of p-toluenesulfonic acid and heated for 30 minutes to 80° C. Then the mixture is poured into ice water, made alkaline with ammonia and extracted with dichloromethane. After washing and drying the mixture is concentrated under vacuum. The thus-obtained crude product is chromatographed on silica gel, yielding 920 mg of 17β-hydroxy-17α-(3-hydroxypropyl)-11β-isopropenyl-4,9-estradien-3-one.

$[\alpha]_D - 70°$.

(b) At −10° C., 3.6 ml of Jones solution is added dropwise to a solution of 620 mg of 17β-hydroxy-17α-(3-hydroxypropyl)-11β-isopropenyl-4,9-estradien-3-one in 35 ml of acetone and the mixture is agitated at this temperature for 30 minutes. Then the mixture is combined with a small amount of methanol, diluted with ethyl acetate and washed with water. After drying over sodium sulfate and concentration, the resultant crude product is chromatographed on silica gel, yielding 375 mg of 19-nor-3-oxo-11β-isopropenyl-17α-pregna-4,9-diene-21,17-carbolactone.

$[\alpha]_D = -38°$.

EXAMPLE 3

(a) A solution of 7.7 g of 3,3-(2,2-dimethyltrimethylenedioxy)-11β-methyl-17α-[(3-tetrahydropyranyloxy)propyl-]-9-estrene-5α,17β-diol in 300 ml of 90% aqueous ethanol is combined with 0.1 g of p-toluenesulfonic acid and agitated for 40 minutes at 75° C. Subsequently the mixture is poured into ice water, rendered alkaline with ammonia, and extracted with dichloromethane. After washing with water and drying over sodium sulfate, the mixture is concentrated under vacuum. The resultant crude product is chromatographed on silica gel, thus producing 4.85 g of 17β-hydroxy-17α(3-hydroxypropyl)-11β-methyl-4,9-estradien-3-one. $[\alpha]_D = -109.1°$.

(b) A solution of 4.8 g of 17β-hydroxy-17α-(3-hydroxypropyl)-11β-methyl-4,9-estradien-3-one in 270 ml of acetone is combined at −70° C. with 27 ml of Jones solution and agitated at this temperature for 30 minutes. Then the mixture is combined with a small amount of methanol and exhaustively concentrated under vacuum, diluted with ethyl acetate, washed with water, dried over sodium sulfate and concentrated under vacuum. The thus-obtained crude product is chromatographed over silica gel, yielding 1.6 g of 11β-methyl-19-nor-3-oxo-17α-pregna-4,9-diene-21,17-carbolactone, mp 198°–201° C.

EXAMPLE 4

(a) Under the conditions described in Example 3(a), 3.3 g of 3,3-(2,2-dimethyltrimethylenedioxy)-11β-ethyl-17α-(3-tetrahydropyranyloxy)propyl]-9-estrene-5α,17β-diol yields 1.45 g of 11β-ethyl-17β-hydroxy-17α-(3-hydroxypropyl)-4,9-estradiene-3-one.

(b) Under the conditions set forth in Example 3(b), 1.35 g of 11β-ethyl-17β-hydroxy-17α-(3-hydroxypropyl)-4,9-estradien-3-one yields 620 mg of 11β-ethyl-19-nor-3-oxo-17α-pregna-4,9-diene-21,17-carbolactone. $[\alpha D]_D = -94.1°$.

EXAMPLE 5

(a) Under the conditions indicated in Example 3(a), 2.1 g of 3,3-(2,2-dimethyltrimethylenedioxy)-11β-propyl-17α-[(3-tetrahydropyranyloxy)propyl]-9-estrene-5α,17β-diol yields 1.2 g of 17β-hydroxy-17α-(3-hydroxypropyl)-11β-propyl-4,9-estradien-3-one. $[\alpha]_D = -52.3°$.

(b) Under the conditions set forth in Example 3(b), 1 g of 17β-hydroxy-17α-(3-hydroxypropyl)-11β-propyl-4,9-estradien-3-one yields 520 mg of 19-nor-11β-propyl-3-oxo-17α-pregna-4,9-diene-21,17-carbolactone. $[\alpha]_D = -70°$.

EXAMPLE 6

(a) Under the conditions described in Example 3(a), 2.8 g of 11β-cyclopropyl-3,3-(2,2-dimethyltrimethylenedioxy)-17α-[(3-tetrahydropyranyloxy)propyl]-9-estrene-5α,17β-diol yields 1.45 g of 11β-cyclopropyl-17β-hydroxy-17α-(3-hydroxypropyl)-4,9-estradien-3-one.

(b) Under the conditions disclosed in Example 3(b), 1.35 g of 11β-cyclopropyl-17β-hydroxy-17α-(3-hydroxypropyl)-4,9-estradien-3-one yields 870 mg of 11β-cyclopropyl-19-nor-3-oxo-17α-pregna-4,9-diene-21,17-carbolactone, mp 156°–158° C.

EXAMPLE 7

(a) Under the conditions described in Example 3(a), 700 mg of 11β-cyclopentyl-3,3-(2,2-dimethyltrimethylenedioxy)-17α-[(3-tetrahydropyranyloxy)propyl]-9-estrene-5α,17β-diol yields 312 mg of 11β-cyclopentyl-17β-hydroxy-17α-(3-hydroxypropyl)-4,9-estradien-3-one.

$[\alpha]_D = -101.6°$.

(b) Under the conditions set forth in Example 3(b), 270 mg of 11β-cyclopentyl-17β-hydroxy-17α-(3-hydroxypropyl)-4,9-estradien-3-one produces 154 mg of 11β-cyclopentyl-17β-hydroxy-19-nor-3-oxo-17α-pregna-4,9-diene-21,17-carbolactone.

$[\alpha]_D = -38°$.

EXAMPLE 8

A solution of 695 mg of 11β-cyclopropyl-3,3-(2,2-dimethyltrimethylenedioxy)-17α-[3-(tetrahydropyranyloxy)-1-(Z)-propenyl-9-estrene-5α,17β-diol in 11 ml of ethanol is stirred for 30 minutes at 55° C. with 71 mg of pyridinium tosylate. Then the mixture is diluted with dichloromethane, washed with sodium bicarbonate solution and water and concentrated under vacuum. The thus-obtained crude product is chromatographed on silica gel, yielding 470 mg of 11β-cyclopropyl-17β-hydroxy-17α-(3-hydroxy-1-Z-propenyl)-4,9-estradien-3-one as a foam.

$[\alpha]D = -69.1°$.

EXAMPLE 9

Under the conditions given in Example 3, 2.7 g of 3,3-(2,2-dimethyltrimethylenedioxy)-5α-hydroxy-11β-methyl-15β,16β-methylene-19-nor-17α-pregn-9-ene-21,17-carbolactone yields 1.2 g of 11β-methyl-15β,16β-methylene-3-oxo-19-nor-17α-pregna-4,9-diene-21,17-carbolactone.

IR: 1760, 1660 cm$^{-1}$.
UV: $\epsilon_{301} = 20,050$.

EXAMPLE 10

Under the conditions indicated in Example 3, 1.9 g of 3,3-(2,2-dimethyltrimethylenedioxy)-5α-hydroxy-15β,16β-methylene-11β-vinyl-19-nor-17α-pregn-9-ene-21,17-carbolactone yields 870 mg of 15β,16β-methylene-3-oxo-11β-vinyl-19-nor-17α-pregna-4,9-diene-21,17-carbolactone.

IR: 1760, 1660 cm$^{-1}$.
IR: $\epsilon_{300}=1750$.

EXAMPLE 11

Under the conditions stated in Example 3, 1.8 g of 11β-cyclopropyl-3,3-(2,2-dimethyltrimethylenedioxy)-5α-hydroxy-15β,16β-methylene-19-nor-17α-pregn-9-ene-21,17-carbolactone yields 720 mg of 11β-cyclopropyl-15β,16β-methylene-3-oxo-19-nor-17α-pregna-4,9-diene-21,17-carbolactone.

IR: 1760, 1660 cm$^{-1}$.
UV: $\epsilon_{302}=20,450$.

EXAMPLE 12

(a) Under ice cooling, 2 g of 3,3-(2,2-dimethyltrimethylenedioxy)-15β,16β-methylene-estra-5(10),9(11)-dien-17-one in 25 ml of tetrahydrofuran (THF) is added dropwise to a solution, prepared from 0.93 g of magnesium and 3.7 ml of allyl bromide, of allylmagnesium bromide in ether. The mixture is then stirred for one hour at room temperature. For working up purposes, the mixture is combined with saturated ammonium chloride solution, diluted with ether, washed with water and saturated sodium chloride solution and dried over sodium sulfate. After concentrating under vacuum, 2.42 g of 3,3-(2,2-dimethyltrimethylenedioxy)-15β,16β-methylene-17α-(2-propenyl)estra-5(10),9(11)-dien-17β-ol is obtained.

(b) A solution of 2.25 g of 3,3-(2,2-dimethyltrimethylenedioxy)-15β,16β-methylene-17α-(2-propenyl)estra(10),9(11)-dien-17α-ol in 35 ml of absolute THF is combined dropwise with a solution of 1.91 g of 9-borabicyclo-3.3.1]nonane in 32 ml of absolute THF; the mixture is agitated overnight at room temperature. Then a solution of 53 mg of sodium hydroxide in 7 ml of water and 3.16 ml of 0% strength hydrogen peroxide is added dropwise thereto and the mixture is refluxed for one hour. To work up the mixture, it is diluted with ethyl acetate, washed with water and saturated sodium chloride solution and concentrated under vacuum, yielding 1.65 g of 3,3-(2,2-dimethyltrimethylenedioxy)-15β,16β-methylene-17α-(3-hydroxypropyl)estra-5(10),9(11)-dien-17α-ol.

(c) Under the conditions indicated in Example 3(b), 1.6 g of 3,3-(2,2-dimethyltrimethylenedioxy)-15β,16β-methylene-17α-(3-hydroxypropyl)estra-5(10),9(11)-dien-17β-ol yields 1.05 g of 3,3-(2,2-dimethyltrimethylenedioxy)-15β,16β-methylene-19-nor-17α-pregna-5(10),9(11)-diene-21,17carbolactone.

(d) A solution of 1.0 g of 3,3-(2,2-dimethyltrimethylenedioxy)-15β,16β-methylene-19-nor-17α-pregna-5(10),9(11)-diene-21,17-carbolactone in 50 ml of methanol is stirred with 6 ml of water and 900 mg of oxalic acid for 17 hours at 50° C., made alkaline with ammonia, and extracted with dichloromethane. After washing with water and drying over sodium sulfate, the resultant crude product is purified by column chromatography on silica gel, thus obtaining 525 mg of 15β,16β-methylene-3-oxo-19-nor-17α-pregna-4,9-diene-21,17-carbolactone, mp 201°-204° C.

UV: $\epsilon_{302}=21,200$.
IR: 1760, 1660 cm$^{-1}$.

EXAMPLE 13

(a) A solution of 1.5 g of 3,3-(2,2-dimethyltrimethylenedioxy)-15β,16β-methylene-19-nor-17α-pregna-5(10),9(11)-diene-21,17-carbolactone in 15 ml of 25% aqueous acetic acid is stirred overnight, diluted with water, extracted with dichloromethane, washed with sodium bi-carbonate solution and water, dried and concentrated under vacuum, yielding 1.35 g of 15β,16β-methylene-3-oxo-19-nor-17α-pregna-5(10),9(11)-diene-21,17-carbolactone.

UV: $\epsilon_{242}=17,700$.
IR: 1760, 1715 cm$^{-1}$.

(b) A solution of 1.2 g of 15β,16β-methylene-3-oxo-19-nor-17α-pregna-5(10),9(11)-diene-21,17-carbolactone in 40 ml of benzene is stirred with 1.2 g of DDQ for 10 minutes at room temperature, the resultant precipitate is filtered off, the filtrate is washed with water, sodium bicarbonate solution and water, dried, and concentrated under vacuum. The resultant crude product is purified by column chromatography on silica gel, thus obtaining 720 mg of 15β,16β-methylene-3-oxo-19-nor-17α-pregna-4,9,11-triene-1,17-carbolactone.

IR: 1760, 1660 cm$^{-1}$.
UV: $\epsilon_{341}=28,100$.

EXAMPLE 14

(a) A solution of 1.7 g of 3,3-(2,-dimethyltrimethylenedioxy)-15β,16β-methylene-17α-(3-hydroxypropyl)-11β-vinylestr-9-ene-5α,17β-diol in 15 ml of pyridine is combined with 1.2 g of p-toluenesulfonic acid chloride and stirred for 16 hours at room temperature. Then the mixture is diluted with dichloromethane, washed with water and concentrated under vacuum. The thus-produced crude product is purified by column chromatography on silica gel, yielding 1.35 g of 3,3-(2,2-dimethyltrimethylenedioxy)-5α-hydroxy-15β,16β-methylene-11β-vinylestr-9-ene [17(β-1')spiro-5']perhydrofuran.

(b) Under the conditions described in Example 3(a), 1.25 g of 3,3-(2,2-dimethyltrimethylenedioxy)-5α-hydroxy-15β,16β-methylene-11β-vinylestr 9-ene[17(β-1')spiro-5']perhydrofuran yields 775 mg of 15β,16β-methylene-3-oxo-11β-vinyl-4,9-estradiene[17(β-1')spiro-5']perhydrofuran.

EXAMPLE 15

(a) Under the conditions described in direction (3), 12 g of 3,3-(2,2-dimethyltrimethylenedioxy)-5α,10α-epoxy-15β,16β-methylene-17α-(3-hydroxypropynyl-)estr-9(11)-en-17β-ol yields 8.4 g of 3,3-(2,2-dimethyltrimethylenedioxy)-17α-(3-hydroxypropynyl)-15β,16β-methylene-11β-vinylestr-9-ene-5α,17β-diol.

(b) Under the conditions set forth in Example 12(d), 8.3 g of 3,3-(2,2-dimethyltrimethylenedioxy)-17α-(3-hydroxypropynyl)-15β,16β-methylene-11β-vinylestr-9-ene-5α,17β-diol produces 6.2 g of 17β-hydroxy-17α-(3-hydroxypropynyl)-15β,16β-methylene-11β-vinylestra-4,9-dien-3-one.

(c) A solution of 6.1 g of 17β-hydroxy-17α-(3-hydroxypropynyl)-15β,16β-methylene-11β-vinylestra-4,9-dien-3-one in 120 ml of THF is hydrogenated with 3 g of Lindlar catalyst. After absorption of one equivalent of hydrogen, the mixture is filtered off from the catalyst, concentrated under vacuum, and the resultant crude product is chromatographed on silica gel, thus obtaining 4.9 g of 17β-hydroxy-17α-(3-hydroxypropenyl)-15β,16β-methylene-11β-vinyl-4,9-estradien-3-one.

EXAMPLE 16

Under the conditions described in Example 3(b), 2 g of 17β-hydroxy-17α-(3-hydroxypropenyl)-15β,16β-methylene-11β-vinylestra-4,9-dien-3-one yields 1.15 g of 15β,16β-methylene-3-oxo-11β-vinyl-19-nor-17α-pregna-4,9,20-triene-21,17-carbolactone.

IR. 1735, 1660 cm$^{-1}$.

EXAMPLE 17

Under the conditions set forth in Example 14(a), 2 g of 17β-hydroxy-17α-(3-hydroxypropenyl)-15β,16β-methylene-11β-vinylestra-4,9-dien-3-one yields 1.54 g of 15β,16β-methyl-ene-3-oxo-11β-vinyl-4,9-estradiene[17(β-1')spiro-5']-1',2'-dihydrofuran.

EXAMPLE 18

A solution of 500 mg of 15β,16β-methylene-3-oxo-11β-vinyl-19-nor-17α-pregna-4,9-diene-21,17-carbolactone in 10 ml of THF is combined with 100 mg of lithium aluminum hydride and stirred for 2 hours at room temperature. Then the mixture is diluted with ethyl acetate, washed with dilute sulfuric acid and water and concentrated under vacuum. The resultant crude product is taken up in 25 ml of CH$_2$Cl$_2$ and stirred overnight with 5 g of manganese dioxide. After the manganese dioxide has been removed by filtration, the thus-obtained crude product is chromatographed on silica gel, yielding 285 mg of 17β-hydroxy-17α-(3-hydroxypropyl)-15β,16β-methylene-11β-vinyl-4,9-estradien-3-one.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 17-substituted estradiene or estratriene of the formula

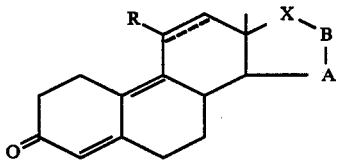

wherein

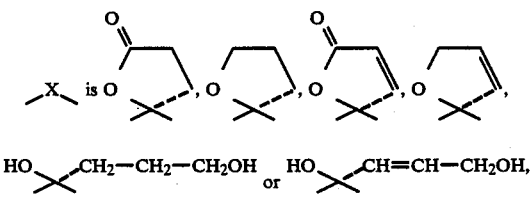

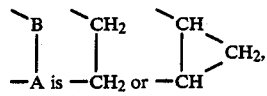

R is alkyl, alkenyl or cycloalkyl each of up to 5 carbon atoms, when

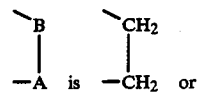

R is hydrogen or alkyl, alkenyl or cycloalkyl each of up to 5 carbon atoms, when

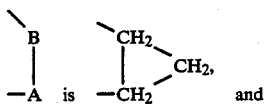

and

a CC-single or CC-double bond.

2. A compound of claim 1, wherein

is a C—C double bond.

3. A compound of claim 1, wherein

is a C—C single bond.

4. A compound of claim 1, wherein R is alkenyl.
5. A compound of claim 1, wherein R is cycloalkyl.
6. A compound of claim 1, wherein R is alkyl.
7. A compound of claim 1, wherein R is methyl, ethyl or vinyl.
8. A compound of claim 1, wherein

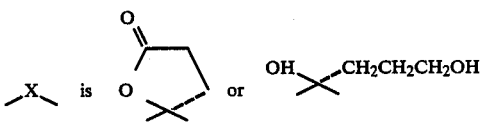

9. 17β-Hydroxy-17α-(3-hydroxypropyl)-11β-vinyl-4,9-estradien-3-one, or 19-nor-3-oxo-11β-vinyl-17α-pregna-4,9-diene-21,17-carbolactone, each a compound of claim 1.

10. 17β-Hydroxy-17α-(3-hydroxypropyl)-11β-isopropenyl-4,9-estradien-3-one, or 19-nor-3-oxo-11β-isopropenyl-17α-pregna-4,9-diene-21,17-carbolactone, each a compound of claim 1.

11. 17α-Hydroxy-17α-(3-hydroxypropyl)-11β-methyl-4,9-estradien-3-one, or 11β-methyl-19-nor-3-oxo-17α-pregna-4,9-diene-21,17-carbolactone, each a compound of claim 1.

12. 11β-Ethyl-17β-hydroxy-17α-(3-hydroxypropyl)-4,9-estradien-3-one, or 11β-ethyl-19-nor-3-oxo-17α- pregna-4,9-diene-21,17-carbolactone, each a compound of claim 1.

13. 17β-Hydroxy-17α-(3-hydroxypropyl)-11β-propyl-4,9-estradien-3-one, or 19-nor-11β-propyl-3-oxo-17α-pregna-4,9-diene-21,17-carbolactone, each a compound of claim 1.

14. 11β-Cyclopropyl-17β-hydroxy-17α-(3-hydroxypropyl)-4,9-estradien-3-one, or 11β-cyclopropyl-19-nor-3-oxo-17α-pregna-4,9-diene-21,17-carbolactone, each a compound of claim 1.

15. 11β-Cyclopentyl-17β-hydroxy-17α-(3-hydroxypropyl)-4,9-estradien-3-one, or 11-cyclopentyl-17β-hydroxy-19-nor-3-oxo-17α-pregna-4,9-diene-21,17-carbolactone, each a compound of claim 1.

16. 11β-Methyl-15β,16β-methylene-3-oxo-19-nor-17α-pregna-4,9-diene-21,17-carbolactone, 15β,16β-methylene-3-oxo-11β-vinyl-19-nor-17α-pregna-4,9-diene-21,17-carbolactone, 11β-cyclopropyl-15β,16β-methylene-3-oxo-19-nor-17α-pregna-4,9-diene-21,17-carbolactone, or 15β,16β-methylene-3-oxo-19-nor-17α-pregna-4,9-diene-21,17-carbolactone, each a compound of claim 1.

17. 15β,16β-Methylene-3-oxo-11β-vinyl-4,9-estradiene-[17(β-1')spiro-5']perhydrofuran, 17β-hydroxy-17α-(3-hydroxypropenyl)-15β,16β-methylene-11β-vinyl-4,9-estradien-3-one, 15β, 16β-methylene-3-oxo-11β-vinyl-19-nor-17α-pregna-4,9,20-triene-21,17-carbolactone, 15β,16β-methylene-3-oxo-11β-vinyl-4,9-estradiene[17(β'1')-spiro-5']-1',2'-dihydrofuran, or 17β-hydroxy-17α-(3-hydroxypropyl)-15β,16β-methylene-11β-vinyl-4,9-estradien-3-one, each a compound of claim 1.

18. 11β-Cyclopropyl-17β-hydroxy-17α(3-hydroxy-1-Z-propenyl)-4,9-estradien-3-one, a compound of claim 1.

19. A pharmaceutical composition comprising a compound of claim 1, and a pharmaceutically acceptable carrier.

20. A pharmaceutical composition comprising 0.5–5 mg of a compound of claim 1 and a pharmaceutically acceptable carrier.

21. A pharmaceutical composition useful for oral contraception comprising effective amounts of a compound of claim 1 as gestagen and of an estrogenic compound as estrogen and a pharmaceutically acceptable carrier.

22. A composition of claim 21, wherein the amount of said gestagen is 0.5 to 5 mg and the amount of the estrogenic compound is equivalent to 0.03–0.05 mg of ethynylestradiol.

23. In a method of achieving a contraceptive effect in a woman of child-bearing age comprising administering 0.5 to 5 mg of a gestagen and an amount of an estrogen equivalent to 0.03 to 0.05 mg of ethynylestradiol to the woman, the improvement wherein the gestagen is a compound to claim 1.

24. A method of treating a headache, depression, water retention or mastodynia occurring as premenstrual symptoms in a woman comprising administering to the woman an effective amount of a compound of claim 1 and a pharmaceutically acceptable carrier.

25. 15β,16β-Methylene-3-oxo-19-nor-17α-pregna-4,9,11-triene-21,17-carbolactone, a compound of claim 1.

26. 17β,hydroxy-17α-(3-hydroxypropyl)-15β,16β-methylene-11β-vinyl-4,9-estradien-3-one, a compound of claim 1.

27. A compound of claim 1, wherein -X- is

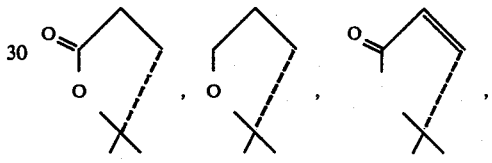

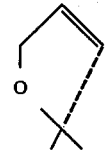

* * * * *